United States Patent
Schuler et al.

(10) Patent No.: US 6,902,548 B1
(45) Date of Patent: Jun. 7, 2005

(54) **USE OF *STREPTOMYCES HYALUROLYTICUS* ENZYME IN OPHTHALMIC TREATMENTS**

(76) Inventors: Ed Schuler, 9117 Three Notch Rd., Troy, VA (US) 22474; Christopher Schuler, 9117 Three Notch Rd., Troy, VA (US) 22474

( * ) Notice: Subject to any disclaimer, the term of this patent is extended or adjusted under 35 U.S.C. 154(b) by 377 days.

(21) Appl. No.: 09/811,754

(22) Filed: Mar. 19, 2001

(51) Int. Cl.$^7$ .............................................. A61M 35/00
(52) U.S. Cl. ................ 604/289; 424/78.04; 424/94.62; 424/429; 604/290
(58) Field of Search ............................... 604/500, 521, 604/27, 28, 289, 290, 294–302; 424/94.1, 424/93.43, 427, 423, 428, 429, 94.62, 78.02, 424/78.04; 623/4.1, 6.11; 435/252.35, 253.5, 435/886, 201, 203

(56) References Cited

U.S. PATENT DOCUMENTS

| | | | |
|---|---|---|---|
| 3,728,223 A | * | 4/1973 | Kaneko et al. ................ 195/62 |
| 4,759,746 A | * | 7/1988 | Straus .......................... 604/51 |
| 4,820,516 A | * | 4/1989 | Sawyer et al. ............ 424/94.62 |
| 5,626,865 A | * | 5/1997 | Harris et al. ................. 424/427 |
| 5,788,957 A | | 8/1998 | Harris |
| 5,792,103 A | * | 8/1998 | Schwartz et al. ............. 604/82 |
| 5,866,120 A | * | 2/1999 | Karageozian et al. .... 424/94.62 |
| 6,037,144 A | * | 3/2000 | Fedorov et al. ............ 435/68.1 |
| 6,039,943 A | | 3/2000 | Karageozian et al. |

FOREIGN PATENT DOCUMENTS

| | | | | |
|---|---|---|---|---|
| WO | WO 00/66139 | * | 11/2000 | .......... A61K 38/00 |

OTHER PUBLICATIONS

Knepper PA et al., Exogenous hyaluronidases and degradation of hyaluronic acid in the rabbit eye, Mar. 1984, Investigative Ophthamology and Visual Science, 25 (3): 286-293. (Abstract only).*

* cited by examiner

Primary Examiner—Jennifer J. Maynard
(74) Attorney, Agent, or Firm—Jagtiani & Guttag

(57) ABSTRACT

A highly specific and easily purified form of hyaluronidase is described for use in ophthalmic treatments. The enzyme, from *Streptomyces hyalurolyticus* is specific for hyaluronidase and carries out an elimination reaction that results in the production of double bonds at the nonreducing end of hyaluronic acid. Hyaluronidase from *Streptomyces hyalurolyticus* has a higher activity than comparable enzymes from other species. The enzyme is now capable of being purified in what is essentially a protease-free form making it applicable to medical treatments. The use of this source of hyaluronidase in ophthalmic treatments is now made possible by its high activity, specificity for hyaluronidase and purity.

10 Claims, No Drawings

USE OF *STREPTOMYCES HYALUROLYTICUS* ENZYME IN OPHTHALMIC TREATMENTS

FIELD OF THE INVENTION

The instant invention relates to the field of enzyme therapy, specifically the use of high purity hyaluronidase from *Streptomyces hyalurolyticus* for the treatment of ophthalmic disorders.

DESCRIPTION OF THE PRIOR ART

Hyaluronidase is a well-known enzyme with a variety of applications. Hyaluronidase is naturally occurring and breaks down various mucopolysaccharides such as hyaluronic acid and the chondroitin sulfates. It is found as a family of enzymes and comes in both monomeric and oligomeric forms. The enzyme presents itself over a broad range of molecular weights and specificities. It is commercially available from a variety of sources including calf or sheep testes, helminthes, leeches, bee venom, snake venom and bacterial sources such as *Streptomyces* and *Streptococcal* species. Various suppliers including REANAL Company, Serva and Sigma Chemical Company produce and distribute hyaluronidase from mammalian sources. A common form of the enzyme, known as Wydase®, is available from Wyeth-Ayerst Laboratories, Inc. Philadelphia, Pa. Wydase® is a preparation of purified bovine testicular hyaluronidase that contains various impurities including proteolytic enzymes.

Wydase® is currently used to prepare the eye for treatment of a variety of ophthalmic disorders. Hyaluronic acid, one substrate for hyaluronidase, is a polysaccharide widely found in the extracellular connective tissue of animals. It is also the primary constituent of the vitreous of the eye. Diabetic retinopathy, trauma to the eye and other disorders of the eye can cause rupture of the retinal blood vessels or leakage from these vessels, which results in blood entering the vitreous humor. The vitreous humor can then become cloudy after such intravitreal hemorrhage. In certain cases, intravitreal hemorrhage can lead to further complications that require quick diagnosis and surgical repair. Such complications can include retinal detachment and formation of fibrous tissue at the site of hemorrhage. Vision may become reduced or even totally impaired in this event, thus it is imperative to treat the hemorrhage and remove the opacity that contributes to such risk. Bovine testicular hyaluronidase is injected into the vitreous humor to remove hemorrhagic blood and clarify the vitreous humor prior to transvitreal viewing of the retina or further treatment of the detached portion. Karageozian et al in U.S. Pat. No. 5,866,120 and U.S. Pat. No. 6,039,943 describe the use of bovine testicular hyaluronidase for this purpose. These patents and the methods described therein are incorporated by reference as though reproduced in their entirety.

In another use, hyaluronidase is used to soften the cornea of the eye in a form of orthokeratology or vision correction. This treatment is commonly referred to as enzyme orthokeratology. Harris in U.S. Pat. No. 5,788,957 and U.S. Pat. No. 5,626,865 describes the use of bovine hyaluronidase to soften the cornea prior to refractive correction. This patent and the methods described are incorporated by reference as though reproduced in its entirety.

Hyaluronidase has also been used to reduce intraocular pressure in the eyes of glaucoma patients through degradation of the hyaluronic acid within the vitreous humor. This application is described in U.S. Pat. No. 4,820,516 to Sawyer and Edwards.

In another version of ophthalmic enzymology, hyaluronidase is added extraocularly as a means for spreading local anesthesia more effectively through tissue prior to surgical interventions. This use as a "spreading agent" also applies to the application of drugs for the treatment of ocular diseases.

Finally, in an optometric use of hyaluronidase, Fedorov et al in U.S. Pat. No. 6,037,144 describe the use of hyaluronidase for preparing artificial lenses. The method comprises steps of providing collagen-containing cattle basal membrane, incubating the membrane in a mixture of pepsin, hyaluronidase and acetic acid and separating the collagen from the mixture. After conditioning, the collagen can be mixed with monomers and polymerized to produce strong, elastic intraocular lenses and contact lenses that are highly biocompatible and gas permeable.

A form of the hyaluronidase from the bacterium *Streptomyces hyalurolyticus* was described in U.S. Pat. No. 3,728,223 to Kaneko et al, which is incorporated by reference as though reproduced in its entirety. The *S. hyalurolyticus* enzyme is currently in use in the health food and animal feed industries but has not been considered applicable to the medical field because of its susceptibility to proteolytic inactivation.

It is clear that hyaluronidase has multiple uses for treating disorders of the eye, yet the commonly used source of surgical hyaluronidase, bovine testes, represents an inefficient source due to its activity and specificity, contamination by unwanted molecules such as proteases and by the complicated process required to purify the enzyme for clinical use. In an analysis of the Wydase® hyaluronidase for contaminants, protease activity ranging from 0.0216 units per mL to 0.0593 units per mL was found depending on the lot tested. This contamination was found in enzyme lots that had hyaluronidase activities ranging from 2.44 turbidity-reducing units (TRU) per mL to 4.82 TRU per mL.

SUMMARY OF THE INVENTION

The invention provides for the use of an alternative source of hyaluronidase, purified from *Streptomyces hyalurolyticus*, for the treatment of ophthalmic disorders. The *S. hyalurolyticus* hyaluronidase requires fewer steps to achieve higher purity and has specificity for hyaluronic acid and not other glycosaminoglycans. The enzyme can be effectively used in medical techniques when contaminating protease is not a concern such as treatments of the eye. These advantages make this bacterially derived hyaluronidase more effective and less expensive for ophthalmic applications.

The enzyme is prepared from the bacterium, *Streptomyces hyalurolyticus*. Growth of bacteria in large-scale culture is inexpensive and preparation of the enzyme requires fewer steps than the mammalian forms. The bacterial preparation provides a form of the enzyme with significantly less contamination from protease, mammalian virus, immunogens and other unwanted particles than other commercially available sources. Use of the *S. hyalurolyticus* enzyme in the eye and particularly in the vitreous humor to prepare intravitreal hemorrhage for treatment is ideal because of its high activity levels relative to other sources of the enzyme and because of its specificity for hyaluronic acid. Because of this high relative activity, a lower concentration of the enzyme is required and the cost to the user is reduced. Furthermore, protease levels in the mammalian eye and vitreous humor are extremely low and do not interfere with the activity of the bacterial enzyme, making the enzyme an ideal candidate for ophthalmic and optometric uses in humans. The hyaluronidase obtained from the S. hyalurolyticus source provides substantial economic and medical advantages over enzyme obtained from mammalian sources.

DETAILED DESCRIPTION OF THE INVENTION

Hyaluronidase is a naturally occurring enzyme that breaks down mucopolysaccharides. The enzyme is derived from a variety of sources but is primarily derived from calf testes for biomedical use. Other sources include sheep testes, helminthes, leeches, bee venom, snake venom and bacteria such as *Streptomyces* and *Streptococcal* species. Depending on the source, the enzyme's substrate specificity varies. Although the preferred source of the enzyme, bovine testes, is currently used in some medical applications, the purification sequence necessary to use the enzyme is laborious and not always effective at producing high purity or high activity enzyme.

Production of a stable hyaluronidase from a bacterial source was attempted as early as the 1970's, and it was reported that a specific strain of the genus *Streptomyces, S. hyalurolyticus* produced hyaluronidase (Biochimica Biophysica Acta. 198 (1970) 607–609). Hyaluronidase from *S. hyalurolyticus* has the advantage of being specific for hyaluronic acid alone and not the other glycosaminoglycans. This enzyme carries out an elimination reaction that results in the production of double bonds at the nonreducing end of hyaluronic acid. However, this new hyaluronidase was determined to be unstable due to inactivation by protease, and accordingly was not considered sufficient for use as a therapeutic enzyme. In particular, contamination by protease or use in systems where proteases are inherent rendered the enzyme inactive and made its medical use prohibitive. Recently, an improved method for purifying hyaluronidase from *S. hyalurolyticus* was achieved whereby the enzyme activity levels far exceeded the nominal contamination by protease. Additional purification steps are possible to eliminate all protease contaminants and provide a high activity, high purity source of hyaluronidase for medical procedures.

Purification methods for hyaluronidases are well developed and widely distributed in the literature. They include such common techniques as extraction, precipitation, centrifugation, ultrafiltration and chromatography. Production of hyaluronidase from bacterial sources has now been found to be faster and less costly than isolation from mammalian testes and contaminating macromolecules can be more easily avoided in a bacterial system than in tissue extraction.

In an exemplary purification scheme, hyaluronidase produced by *S. hyalurolyticus* is harvested from bacteria grown in a suitable culture medium such as that described in U.S. Pat. No. 3,728,223. The techniques used in the various purification steps are well known in the art and are described in the '223 patent as well as various references in enzymology and protein purification including *Guide to Protein Purification: Methods in Enzymology*, M.P. Deutscher editor, Academic Press 1997. The supernatant from the growth medium is filtered to remove cells and an ultrafiltration step is performed to further remove pigments and other particulate matter. The proteins within the filtrate are precipitated with a first precipitant and filtered then precipitated with a second precipitant and filtered. After dissolution of the final precipitate and filtration with Sephadex, two ion exchange chromatography steps are performed to isolate the hyaluronidase. Dialysis of the isolate is performed to remove salts followed by membrane filtration and freeze-drying. A variety of tests, including polyacrylamide gel electrophoresis, enzyme linked immunosorbent assays and substrate-gel assays are known in the art to determine purity and activity of the hyaluronidase.

The use of hyaluronidase from *S. hyalurolyticus* for medical purposes is still subject to inhibition or deactivation due to the variety of proteolytic enzymes inherent to biological systems. For ophthalmologic uses, particularly those described above, inactivation of the hyaluronidase is minimal due to the small amount of protease found in the vitreous humor. The vitreous humor is greater than 99% water. Less than 1% of the vitreous humor is comprised of macromolecules, particularly substances similar to those found in albumin. Proteolytic enzymes are found in minimal concentrations; these are insufficient to affect the activity of the *S. hyalurolyticus* hyaluronidase. Thus a clear but unexpected advantage exists in using this easily purified and highly active source of hyaluronidase in the eye.

A contaminant analysis of hyaluronidase purified from *S. hyalurolyticus* (Amano Enzyme Company, Nagoya, Japan) demonstrates significantly reduced protease activities in the range of 0.00316 units per mL to 0.0188 units per mL and substantially higher hyaluronidase activities (152 to 218 TRU per mL) than found in the bovine enzyme. The *S. hyalurolyticus* hyaluronidase activity is at least about 10 TRU per mL; whereas, the bovine enzyme hyaluronidase activities range from 2.44 to 4.82 TRU per mL. This means that less *S. hyalurolyticus* enzyme is necessary per treatment. Although the hyaluronidase obtained from *S. hyalurolyticus* is reported to be susceptible to protease inactivation, less contaminating protease means that the enzyme is more stable for ophthalmic use. These advantages of easier and higher yield purification, higher enzyme activity and use in a system that is essentially free from inactivating proteases, make this source of hyaluronidase a better candidate for ophthalmologic uses.

In a preferred use of hyaluronidase purified from *S. hyalurolyticus*, the enzyme is formulated in an injectable thimerosol-free preparation. The enzyme, prepared as a lyophilized powder for injection, is reconstituted in a balanced salt solution, commonly made up of 0.6 to 0.7% sodium chloride, 0.07 to 0.08% potassium chloride, 0.04 to 0.05% calcium chloride dihydrate, 0.02 to 0.04% magnesium chloride hexahydrate, 0.3 to 0.4% sodium acetate trihydrate, 0.1 to 0.2% sodium citrate dihydrate and sodium hydride/hydrochloric acid to adjust the pH to 6.0, then sterile water qs to 100%.

This reconstituted enzyme is injected intravitreally once at six to sixteen days prior to transvitreal viewing of the retina. Dosing is in the range of 50 to 250 IU of hyaluronidase with the preferred dosage being 50 to 100 IU. Clearing of hemorrhage from the vitreous humor occurs over the described times and such clearing is significantly faster than that which would have occurred without hyaluronidase treatment.

In an extraocular use, a single application of the formulation described above can be added topically to the eye fifteen minutes to twelve hours prior to administration of anesthesia. This improves the penetration and efficacy of anesthetics prior to ophthalmic surgery.

In another use, *S. hyalurolyticus* hyaluronidase is used to soften the cornea of the eye prior to enzyme orthokeratology. The technique modifies or degrades the hyaluronic acid-derived structural component of the cornea, allowing the cornea to become softer and more pliable. The cornea can then be reshaped using a contact lens or other means. In this technique, the lyophilized form of *S. hyalurolyticus* hyaluronidase is reconstituted in the carrier solution described above or another pharmaceutically acceptable carrier. Anesthetics such as proparacaine hydrochloride can be included in the solution to anesthetize the cornea. A dose of hyaluronidase appropriate for softening the cornea, typically between 100 and 1500 IU per milligram of substrate, is applied topically and the cornea is allowed to soften prior to reshaping and refractive correction.

In an optometric use of *S. hyalurolyticus* hyaluronidase, the enzyme is used in preparing artificial lenses. Following the disclosure of the '144 patent, the method comprises incubating collagen-containing cattle basal membrane in a mixture of pepsin, hyaluronidase and acetic acid and separating the collagen from the mixture. After conditioning, the collagen is mixed with monomers and polymerized to produce strong, elastic intraocular lenses and contact lenses that are highly biocompatible and gas permeable.

The preceding examples are provided for descriptive purposes solely and are not meant to limit the embodiments of the invention. Other formulations and uses of the *S. hyalurolyticus* hyaluronidase enzyme will become apparent to those of ordinary skill in the art.

What is claimed is:

1. A method for accelerating the clearance of hemorrhagic blood from the vitreous humor of a mammalian eye, comprising the step of injecting into the vitreous humor a solution which contains hyaluronidase from *Streptomyces hyalurolyticus* to provide a dose having a hyaluronidase activity of at least about 10 Turbidity Reducing Units (TRU) of said hyaluronidase, said solution being essentially free of contaminating protease.

2. A method of treating eye disorders comprising the step of applying essentially protease-free hyaluronidase from *Streptomyces hyalurolyticus* to the eye, wherein said hyaluronidase is dissolved in a saline solution, and wherein said treating of said eye disorders is the clearing of hemorrhagic blood from the vitreous humor of a mammalian using an amount of hyaluronidase sufficient to clear the blood.

3. A method of treating eye disorders comprising the step of applying essentially protease-free hyaluronidase from *Streptomyces hyalurolyticus* to the eye, wherein said hyaluronidase is dissolved in a saline solution, and wherein said treating of an eye disorder is the softening the cornea of a mammalian eye prior to refractive correction by using an amount of hyaluronidase sufficient to soften the cornea.

4. A method of treating eye disorders comprising the step of applying essentially protease-free hyaluronidase from *Streptomyces hyalurolyticus* to the eye, wherein said hyaluronidase is dissolved in a saline solution, and wherein said treating of an eye disorder is the spreading local anesthesia more effectively through ocular tissue prior to surgical interventions by using an amount of hyaluronidase sufficient to spread anesthesia.

5. A method of treating eye disorders comprising the step of applying a mixture including essentially protease-free hyaluronidase from *Streptomyces hyalurolyticus* to a collagen-containing membrane, wherein said treating of an eye disorder is the isolating of collagen to produce contact lenses by using hyaluronidase from *Streptomyces hyalurolyticus*.

6. The method of claim 5, wherein said collagen-containing membrane is cattle basal membrane.

7. The method of claim 5, wherein said mixture comprises hyaluronidase from *Streptomyces hyalurolyticus*, pepsin, and acetic acid.

8. A method of treating eye disorders comprising the step of applying essentially protease-free hyaluronidase from *Streptomyces hyalurolyticus* to the eye, wherein said hyaluronidase is dissolved in a saline solution, and wherein said treating of an eye disorder is the stimulating of flow of physiological fluids in the eye which comprises contacting a physiological fluid of the eye with said hyaluroinidase using an amount of hyaluronidase sufficient to stimulate the flow of said fluid.

9. The method of claim 8 wherein the physiological fluid in the eye is contacted for the treatment of glaucoma, thrombosis, detached or impending detached retina, or for the non-surgical removal of obstructions.

10. The method of claim 1, wherein said hyaluronidase activity is in the range of about 152–218 Turbidity Reducing Units (TRU) of said hyaluronidase.

* * * * *